United States Patent [19]
Burrington et al.

[11] Patent Number: 5,986,155
[45] Date of Patent: Nov. 16, 1999

[54] CATALYTIC PROCESS FOR MAKING HIGH REACTIVITY ALKYLATING AGENTS AND PRODUCTS RESULTING THEREFROM

[75] Inventors: James D. Burrington, Mayfield Village; Stuart L. Bartley, Wickliffe; Douglas C. Rhubright, Chardon; Paul A. Lewis, Mentor; Marvin B. DeTar, Wickliffe; Alicia L. Kliever, Mentor; Frank A. Del Greco, Novelty; Lawrence T. Novak, South Euclid, all of Ohio

[73] Assignee: The Lubrizol Corporation, Wickliffe, Ohio

[21] Appl. No.: 08/676,658

[22] Filed: Jul. 10, 1996

[51] Int. Cl.⁶ ............................... C07C 1/00; C07C 2/64; C07C 2/70
[52] U.S. Cl. .................. 585/323; 585/448; 585/449; 585/458; 585/459; 585/462; 585/463; 585/465; 585/466; 585/467
[58] Field of Search ................................ 585/446, 449, 585/458, 466, 467, 448, 459, 462, 463, 465, 323, 450, 671

[56] References Cited

U.S. PATENT DOCUMENTS

| | | | |
|---|---|---|---|
| 3,513,085 | 5/1970 | Leas | 585/315 |
| 3,684,423 | 8/1972 | Chapman | 260/683.51 |
| 3,927,131 | 12/1975 | Ward | 260/654 D |
| 4,046,533 | 9/1977 | Olund | 62/468 |
| 4,072,730 | 2/1978 | Winter, III | 260/671 R |
| 4,524,230 | 6/1985 | Haensel | 585/446 |
| 5,182,247 | 1/1993 | Kuhlmann et al. | 585/671 |
| 5,202,102 | 4/1993 | Nguyen | 208/262.1 |
| 5,434,328 | 7/1995 | Barri et al. | 585/671 |

*Primary Examiner*—Glenn Caldarola
*Assistant Examiner*—In Suk Bullock
*Attorney, Agent, or Firm*—Beverly A. Pawlikowski; David M. Shold

[57] ABSTRACT

Treating low reactivity alkylating agents in the vapor phase with catalysts converts the low reactivity alkylating agents to high reactivity alkylating agents. The alkylating agents are useful in synthesis of alkyl aromatics with Lewis acid catalysts.

8 Claims, No Drawings

CATALYTIC PROCESS FOR MAKING HIGH REACTIVITY ALKYLATING AGENTS AND PRODUCTS RESULTING THEREFROM

BACKGROUND OF THE INVENTION

Friedel-Crafts alkylation of aromatics in the presence of Lewis acids are extremely important reactions in both industrial applications and laboratory synthesis. It is generally thought that alkylation reactions proceed by the attack of a carbonium ion formed from the alkylating agent on the aromatic moiety. Common alkylating agents used with Lewis acids are alkyl halides and alkenes. Other aromatic alkylations which proceed through carbonium ion formation use sulfuric acid, toluene sulfonic acids, and sulfonic acids or resins in the strong acid form with alkenes and alcohols to effect aromatic alkylation.

Problems which may be encountered in alkylation reactions with carbonium ions are that the carbonium ion may rearrange and become less reactive and the alkyl aromatic derived from the rearranged carbonium ion may result. Also, in using a Lewis acid such as $AlCl_3$, the halogen may add to the alkylating agent.

To overcome reactivity problems in alkylation reactions, an excess of alkylating agent is often used. This creates problems in that the recovered residual alkylating agent has lower reactivity than the starting alkylating agent partly due to rearrangement products being formed. Further problems result in Friedel-Crafts alkylation if the alkylating agent is halogenated by the catalyst. The residual alkylating agent may be recovered from the alkylating process. These compounds may be recycled, albeit to form lower yield of alkyl aromatics because of their lower reactivity. They may also be used in other applications such as for fuels. However, depending on the halogen content of the recovered alkylating agents alternate uses may be limited, even for fuel purposes. This could lead to disposal problems including disposal costs for halogenated alkylating agents.

SUMMARY OF THE INVENTION

In this invention, disclosure is made of methods whereby low reactivity alkylating agents are converted into high reactivity alkylating agents. Disclosure is also made of dehydrohalogenation of alkylating agents. Dehydrohalogenation affects both reactivity of alkylating agents, and their alternative uses. The invention describes alkylating agents being passed in the vapor phase over catalysts which function as isomerizing catalysts, dehydrohalogenation catalysts or both.

In passing over the catalysts, a low reactivity alkylating agent is converted to a high reactivity alkylating agent. The low reactivity alkylating agent will yield less than 60% dialkylate in the $AlCl_3$ catalyzed alkylation of diphenylamine. The reaction is described in Example 1 below.

The high reactivity alkylating agent will yield at least 60% dialkylate under the conditions of Example 1.

The alkylating agents are generally low reactivity alkenes. Sources of alkenes for use in this invention include low reactivity alkenes and halogen-containing alkenes as defined above either purchased, synthesized or recovered from alkylating reactions. The alkenes are $C_4$–$C_{24}$ alkenes and halogen containing analogs with the preferred groups being $C_4$–$C_{12}$. It will be understood that the alkylating agents may be mixtures of alkylating compounds. A most preferred low reactivity alkylating agent is nonene which has been recovered from the reaction of nonene with diphenylamine to produce dinonyl diphenylamine as described in Example 1.

The halogen content of the low reactivity alkylating agent may be about 1.0 weight percent or less. Following passing over the dehydrochlorination catalyst, the chlorine content of the alkylating agent is reduced to 0.05 weight percent or less.

The isomerizing and/or dehydrohalogenation catalysts are selected from solid catalysts or catalysts on solid supports. Examples of catalysts include metal oxides, clays, acidified clays, silicas, aluminas, silica aluminas, and zeolites. The preferred catalysts for use in this invention include sulfuric acid activated clay, iron oxide on alumina, or phosphotungstic acid. The acidified clay may be purchased from Engelhard as F-24.

The iron oxide on alumina may be purchased from Engelhard Fe-0301 T1/8". The $FeO_x$ catalyst may be prepared by impregnating an alumina extrudate with ferric nitrate, followed by denitrification and calcination at 400° C.

EXAMPLE 1

Dialkyl Diphenylamine 1000 grams diphenylamine (5.88 moles) is charged to a glass-lined reactor preheated to about 250° F. To this is added with mixing 1043.7 grams nonene (TEXACO) (8.23 moles) and 29.3 grams (0.4 mole) butanol. To the mixture is then added quickly in three portions 100 grams of (0.75 mole) anhydrous aluminum chloride while maintaining the exothermic reaction. The reaction is continued at 290–300° F. A second batch of nonene is added at 290° F., this batch constitutes 972.7 grams (7.72 moles) of nonene. The mole ratio of nonene to diphenylamine is 2.7 to 1. The reaction progress is monitored by NMR and IR analysis as described below.

When infrared analysis shows the reaction to be complete, 26.8 grams 50% sodium hydroxide in 390 ml. water were added to neutralize the mixture. Adjustment in NaOH may be required. The water is separated and the reaction residue washed with water and steam stripped to remove residual nonene. The reaction products are sampled for final analysis and are diluted with oil for storage and future use.

For purposes of this invention, a low reactivity nonene or other alkene alkylating agent is defined as one in which the yield under conditions of Example 1 for ten hours is less than 60% of dialkyldiphenylamine and the high reactivity alkene alkylating agent is one in which the yield is at least 60%. Both low and high reactive species may contain halogen. The yield is based on the conversion of diphenylamine to the dialkylate during the 10 hour period.

Infrared Analysis of Dialkylated Diphenylamine Reaction

The infrared spectra (IR) is run as a thin film and the percent dialkylate in the reaction mixture determined by the following formula:

Percent dialkylate=[Log (ABS of PARA@ 820 $cm^{-1}$/ABS of Mono@ 743 $cm^{-1}$)+1.141]/0.019

The absorbance at 820 $cm^{-1}$ and 743 $cm^{-1}$ correspond to dialkylate and monoalkylate respectively for nonylated diphenylamine. The IR spectral method has good applicability for determining a reaction stopping point for Example 1. That stopping point is where the percent dialkylate value becomes constant. The IR spectra can be run using any IR spectrometer with a FTIR instrument using OBEY programming language being preferred. The analysis is done by means of a thin film sample using 0.025 mm spaced NaCl plates with $IR^3B.OY$ software or a ZnSe ATR contact sampler, with 50° $IR^3BATR.04$ software.

While the IR method outlined above is useful in determining reaction end points and dialkylate percent yields, it has been found that NMR analysis gives greater accuracy in terms of yield and product distribution.

Nuclear Magnetic Resonance Analysis of Dialkylate in Diphenylamine Reaction

In the NMR method, chemical shifts are assigned to NH peaks in various environments and from these peak areas yields of dialkylates can be calculated. NMR spectrum have been recorded in $CDCl_3$ with a FTNMR instrument. NMR peak assignments are as listed below:

| | |
|---|---|
| NH from diphenylamine | 5.6 ppm |
| NH from monoalkylate | 5.53 ppm |
| NH from dialkylate | 5.47 ppm |

The yield of dialkylate based on diphenylamine can be calculated by the areas under the respective peaks.

In Example 1 the residual alkylating agent, nonene in the example above, is recovered. The recovered alkylating agent is tested for reactivity by re-reacting with diphenylamine under the same conditions as Example 1 for 10 hours. At this point, if the reactivity of the recovered alkylating agent is less than 60% as measured by the yield of diphenyl amine, it is possible to increase its reactivity to at least 60% by reacting the low reactivity alkene alkylating agent in the vapor phase with the catalysts of this invention. The low reactivity alkylating agents which may be reacted with the catalysts of this invention include those recovered from an alkylating reaction, commercially-available alkenes, alkenes having a halogen content of 1 percent by weight or less. The latter may be isolated from alkylating reactions using $AlCl_3$.

The catalysts used in this invention are listed above with the preferred catalysts being Englehard F-24, a sulfuric acid activated clay and iron oxide on alumina, Engelhard Fe-0301 T1/8". An iron oxide on alumina was also prepared as outlined below.

Iron Oxide on Alumina Catalyst $Al_2O_3$ (Engelhard Al-3945 E 1/20), 345.70 grams was dried at 200° C. for 48 hours. To the aluminum oxide was added in four portions a total of 800 ml of water containing 86.27 grams of $Fe(No_3)_3.9H_2O$ (20% $Fe(NO_3)_3.9H_2O$) by the incipient wetness technique. The volumes added in the four steps were 244 ml, 233 ml, 179 ml and 146 ml. The $Al_2O_3$ bed was dried for 24 hours at 170° C. between each wetting.

The iron containing $Al_2O_3$ was then heated at 400° C. under air for about 4 hours to convert the iron to iron oxide. The iron oxide content was calculated to be 5% by weight of the catalyst.

Reaction of Alkylating Agents with $Fe_2O_3$ On Alumina and F-24

A residual nonene alkylating agent having 0.1 weight percent chlorine was recovered from the reaction mixture run under the conditions of Example 1. The recovered chlorine containing alkylating agent when re-reacted with diphenylamine for 10 hours yielded about 50% dialkylate under the conditions of Example 1.

A fixed bed reactor was prepared for dehydrochlorination and isomerization of the residual alkylating agent. The reactor consisted of a 10 inch long ¾ inch diameter stainless steel tube containing F-24 or $Fe_2O_3$ on alumina catalysts and in a furnace. The catalyst bed within the tube is 75 cubic centimeters. The residual alkylating agent was heated to vaporization and passed over the catalyst bed. The catalyst treated alkylating agent was recovered in cooling traps and alkylating reactivity determined by reacting the catalyst treated residual alkylating agent with diphenylamine under the conditions of Example 1 for 10 hours to give dialkylated diphenylamine yield of about 70%. The chlorine content of the dehydrochlorinated alkene was 0.005 percent by weight or less.

For chlorine containing residual alkylating agents, treatment with the catalysts of this invention can lower the chlorine content of the alkylating agent to 0.005 weight percent or less depending on the residual time in the catalyst bed, and the temperature of the bed. A temperature of 350° F. is adequate to effect chlorine reduction, but temperature above 450° F. for at least 5 seconds is preferred. However, it was found that to increase the alkylating properties of low reactivity alkylating agents a temperature of 650–700° F. was preferred with a residence time in the reaction of about 10 seconds or less. In operation, a residence time in the catalyst containing reactor of less than about 5 seconds is preferred. This is the preferred temperature range for increasing the alkylating activity of low reactivity commercial alkylating agents, residual alkylating agents isolated following Lewis acid catalyzed alkylating reaction and halogen containing low reactivity alkylating agents.

Catalyst Treatment of Low Reactivity Commercial Alkylating Agent

A commercial nonene yielded 59% dialkylate when reacted for 10 hours with diphenylamine under the conditions of Example 1. The nonene, after passing in the vapor phase over a 75 cc catalyst bed of F-24 at 650° F. for 5 seconds, was converted to a high reactivity alkene which yielded 71% dinonyl diphenylamine under the reaction conditions of Example 1 after 10 hours reaction time.

What is claimed is:

1. A method for making alkylated aromatics, said method comprising the steps of:

(A) reacting alkenes with aromatic compounds in the presence of an alkylating catalyst to produce alkylated aromatic compounds;

(B) separating residual alkenes from the alkylation reaction following formation of said alkylated aromatic compounds;

(C) passing said residual alkenes in the vapor phase over an isomerization catalyst to produce reactive alkenes, said isomerization catalyst being selected from the group consisting of (a) metal oxides, (b) clays, (c) silicas, (d) aluminas, (e) silica-aluminas, (f) zeolites, (g) phosphotungstic acids or supported analogues thereof or mixtures thereof;

(D) reacting said reactive alkenes with aromatic compounds in the presence of an alkylating catalyst to produce alkylated aromatic compounds in a yield greater than the yield obtainable from said residual alkenes.

2. The method according to claim 1, wherein said residual alkenes have chlorine content of 1.0 percent by weight or less.

3. The method according to claim 1, wherein said alkylating catalysts are Lewis acids, proton acids, and ion exchange resins in the acid form.

4. The method according to claim 1, wherein said alkylating catalyst is $AlCl_3$ or $BF_3$.

5. The method according to claim 1, wherein said isomerization catalyst is also a dehydrochlorination catalyst.

6. The method according to claim 1, wherein said reactive alkenes have chlorine content of 0.05 percent by weight or less.

7. The method according to claim 1, wherein said alkenes are $C_4$–$C_{24}$.

8. The method according to claim 1, wherein said alkenes are $C_4$ to $C_{12}$ alkenes.

* * * * *